(12) United States Patent
Butterfield

(10) Patent No.: US 8,302,485 B2
(45) Date of Patent: Nov. 6, 2012

(54) TESTING DEVICE FOR STRESS CORROSION CRACKING

(75) Inventor: Albert Eugene Butterfield, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 218 days.

(21) Appl. No.: 12/914,865

(22) Filed: Oct. 28, 2010

(65) Prior Publication Data

US 2012/0103105 A1    May 3, 2012

(51) Int. Cl.
*G01N 19/08* (2006.01)
(52) U.S. Cl. ......................................................... 73/799
(58) Field of Classification Search .................... 73/856, 73/799
See application file for complete search history.

(56) References Cited

U.S. PATENT DOCUMENTS

| | | | |
|---|---|---|---|
| 3,427,873 A | | 2/1969 | Mehdizadeh |
| 3,504,535 A | * | 4/1970 | Cobb et al. ........................ 73/86 |
| 3,919,884 A | * | 11/1975 | Gunderson et al. ............. 73/831 |
| 5,571,955 A | | 11/1996 | Beavers et al. |
| 5,711,131 A | | 1/1998 | Thomas |
| 7,387,031 B1 | * | 6/2008 | Perrin et al. .................... 73/820 |
| 7,519,481 B2 | | 4/2009 | Perrin et al. |

FOREIGN PATENT DOCUMENTS

| | | |
|---|---|---|
| WO | 57190250 A | 11/1982 |
| WO | 10142186 A | 5/1998 |
| WO | 2005338026 A | 12/2005 |

OTHER PUBLICATIONS

PCT International Search Report and Written Opinion, International Application No. PCT/US2011/051984, dated Mar. 30, 2012, pp. 1-8.
U.S. Appl. No. 12/913,690, filed Oct. 27, 2010, Butterfield.
Low friction hydraulic cylinder for stress-corrosion testsing, Brown et al., Br. Corros. J. 1969, vol. 4. May.
Stress Corrosion Cracking—a new approach to testing method, Dietzel et al., Materials Science, vol. 33, No. 4, 1997.
ASTM G30-97 (Reapproved 2009).
Compact Pneumatically Driven Apparatus for Corrosion Fatigue Tests, Freid et al., Electrochemical Methods in Corrosion research, pp. 263-265, 1984.
Apparatus for Stress Corrosion Tests in Boiling Magnesium Chloride Solution, Streicher et al., Corrosion, NACE vol. 25, No. 1, Jan. 1969.
Pending U.S. Appl. No. 12/913,690, filed Oct. 27, 2010.

* cited by examiner

*Primary Examiner* — Lisa Caputo
*Assistant Examiner* — Octavia Davis-Hollington

(57) ABSTRACT

The present disclosure provides a testing method for stress corrosion testing of materials, e.g., a test specimen, in corrosive materials. The method comprises: providing a test device having: a base configured to house a reservoir for containing the corrosive media and a holder configured to secure the test specimen, the holder includes at least a sleeve to secure the test specimen in place and apply compressive stress against the test specimen, the holder is rotatably connected to the base to lower the test specimen into the reservoir; mounting the test specimen onto the holder; pivoting the holder towards the reservoir to lower at least a portion of the test specimen in the reservoir; adjusting the sleeve to apply a sufficient amount of stress on the test specimen; and filling the reservoir with a sufficient amount of the corrosive media for stress corrosion testing.

20 Claims, 3 Drawing Sheets

TESTING DEVICE FOR STRESS CORROSION CRACKING

TECHNICAL FIELD

The present disclosure provides a stress corrosion testing device and related methods.

BACKGROUND

The corrosive resistance of material can depend on whether the material exposed to the corrosive substance is under stress. In other words, materials that would not otherwise fail when exposed to a corrosive environment can fail if they are exposed to the same environment when under stress. Methods and devices have been developed to test materials to better understand how certain material will perform when exposed to potentially corrosive materials while under stress. Stress corrosion testing devices and methods typically involve evaluating test materials after they have been under stress in a potentially corrosive environment for a period of time.

In many testing applications, it is desirable to make efficient use of the potentially corrosive materials used in the test and to conduct the test in a consistent and controlled manner.

SUMMARY

The present disclosure provides a new stress corrosion testing device and related methods that address these as well as other challenges. In one aspect, the present disclosure provides a device for partially submerging a test specimen in a shallow reservoir of potentially corrosive material. In another aspect, the present disclosure provides a testing method that is easy to employ in a consistent and controlled manner and also makes efficient use of the potentially corrosive materials.

DETAILED DESCRIPTION

Figure 1:
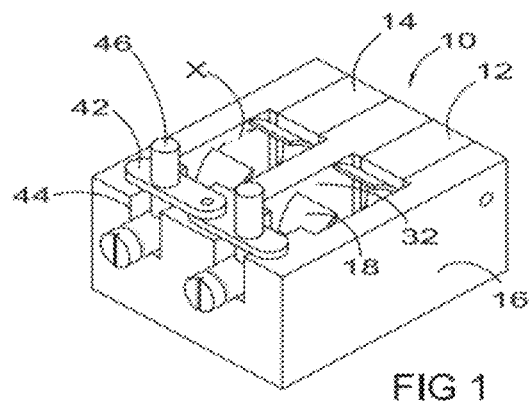
FIG. 1 is a perspective view of a testing device according to the principles of the present disclosure.
Figure 6E:
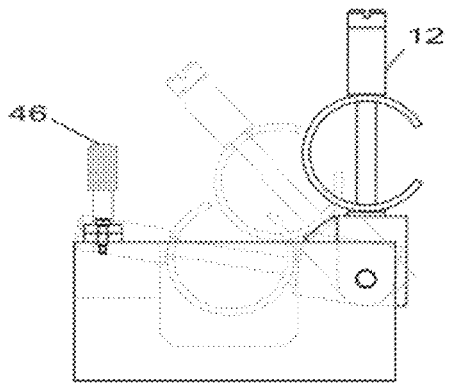
FIG. 6E is a side view of the testing device of FIG. 1, showing various positions of one holder as it is being raised.
Figure 6A:
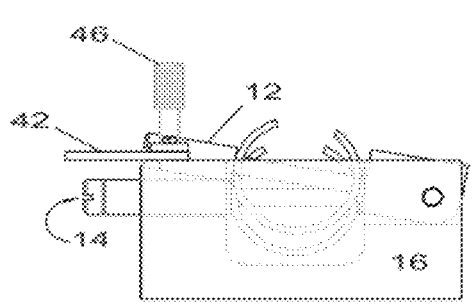
FIG. 6A is a side view of the testing device of FIG. 1 with one holder in a partially raised position.
Figure 6B:
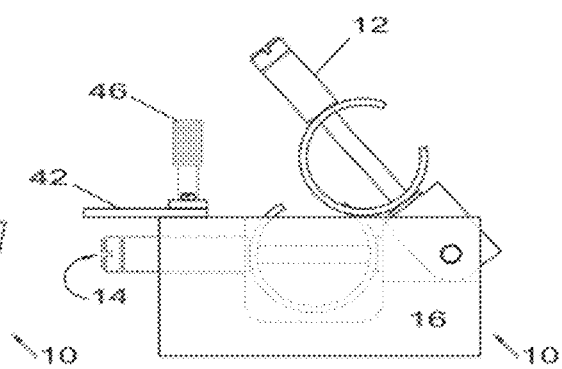
FIG. 6B is a side view of the testing device of FIG. 1 with one holder in a partially raised position.
Figure 6C:
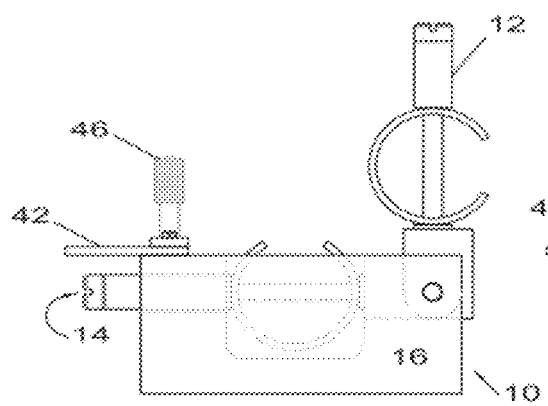
FIG. 6C is a side view of the testing device of FIG. 1 with one holder in a fully raised position.
Figure 6D:
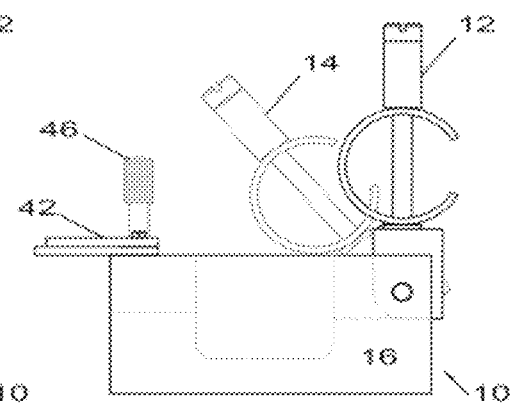
FIG. 6D is a side view of the testing device of FIG. 1 with one holder in a fully raised position and another holder in a partially raised position.

Many professional organizations, e.g., NACE (National Association of Corrosion Engineers) or ASTM (American Society for Testing and Materials), have developed standard test methods for testing materials in corrosion environments, including test methods for stress corrosion cracking (SCC) in specific chemical environments. SCC refers to intergranular or intragranular cracking caused by the simultaneous presence of tensile stress and a corrosive environment. The present disclosure provides a testing device and method that is easy to use in a consistent and controlled manner. In addition, the testing device and method makes efficient use of the potentially corrosive materials and thereby minimizes the amount of test material waste. In one embodiment, the device is for evaluating physical stress that can be applied to a test specimen. In another embodiment, the device is for testing stress corrosion cracking damage in a specimen.

In one embodiment, the testing device comprises a reservoir to hold a corrosive media for testing; a holder to secure the test specimen. In one embodiment with the testing of "heavy" corrosive media, the testing device further comprises a retaining frame for securing the holder in a locked position. In one embodiment, the retaining frame includes a hold-down mechanism, configured to rotate about a horizontal axis from a release position to a locked/stationary position. In the locked position, the holder is held down so that the holder is not free to rotate upwardly. The hold down is particularly useful for testing particularly heavy corrosive media or particularly light specimen such that the specimen would float in the test fluid. The hold down keeps the test specimen submerged in the reservoir.

The holder in one embodiment is configured with bracing means, e.g., bolt or restraining jig, to compress the test specimen. In another embodiment, the holder is configured to rotate around a vertical axis, allowing the test specimen to be taken in and out of the corrosive media. In yet another embodiment, the holder is further provided with a strain gauge to record changes in the stress on the specimen as its properties change with time in the test environment. Examples of strain gauges include electrical gauges or fiber optic gauges. In one embodiment, instruments are provided connected to the device to measure properties including but not limited to the pH and electrochemical properties of the corrosive media.

The specimen can be a C-ring specimen as specified according to NACE, a specimen in a U-bend configuration specified according to ASTM, or other suitable shapes including but not limited to rectangular, circular, cylindrical, double U-bend, or L-shaped. The specimen in one embodiment is a rectangular strip which is bent into the specified shape according to the appropriate test method.

The test device can be of different dimensions. It can be scaled up or down depending on the test specimen for stress testing, small samples according to ASTM or NACE standards, or large pieces of field equipment. The test specimen can also be of different dimensions. The thickness of the specimen can be uniform or vary from one location to another within the test specimen itself. In one embodiment, the thickness ranges from 0.5 mm to 20 mm. In one embodiment of a U-bend (or C-ring) configuration, the radius of the bend ranges from 4 to 100 mm. The dimensions can be significant smaller or larger than listed here, depending on the specifications of the test standard as well as the material being tested.

The reservoir in one embodiment is tailored to conform to the configuration of the specimen being tested, e.g., having a contoured bottom to accommodate the testing of C-ring or U-bend specimen, or having an overall length being slightly longer than the length of the test specimen, and an overall width being slightly wider than the width of the test specimen, thus minimizing the amount of test medium needed. In another embodiment, the reservoir has a square or rectangular configuration. In yet another embodiment, a single reservoir may be configured to receive multiple test specimens of different sizes and configurations.

In one embodiment, the reservoir being constructed in a two-piece configuration with a basin for accommodating an insert liner. The testing device can have a plurality of interchangeable insert liners with the liners being constructed of different materials accommodating different corrosive media to be tested. The interchangeable liners can be of different shapes, configurations, and sizes to accommodate different test specimen. In one embodiment, the liner is configured as multiple "reservoirs" having multiple openings to receive different test specimen in their own "reservoirs." In another embodiment, the insert liner is configured as a single reservoir with a single opening for the testing of multiple test specimens in one reservoir. The holder accordingly can be configured to accommodate multiple test specimen for use with the one single reservoir, or to go into the different reservoirs.

The retaining frame, reservoir and holder can be constructed out of the same material or different material. In one embodiment, the material is an engineering plastic such as polyacetal, polyester, polyvinyl chloride, and the like. In another embodiment, the material is a corrosion resistant high performance alloy such as Hastelloy™ alloy, Nitronic™ super alloy and the like. In one embodiment, the reservoir and frame can be molded or cast as a single piece. In another embodiment, the reservoir and frame can be constructed separately (e.g., an aluminum frame structure supporting a ceramic or glass reservoir).

The device can be used for testing performance of materials, e.g., the test specimen, in a number of corrosive media, e.g., halides, acids, fluids simulating downhole fluids in an oil well. Examples include but are not limited to nuclear waste, polythionic acids (ASTM G 35), magnesium chloride (ASTM G 37), sodium chloride (ASTM G103), crude oil, and mercury. Additives can be added to the corrosive media for testing to determine how additives affect metals in the fluid environment, including but not limited to corrosion inhibitors, biocides, and performance modifiers.

The device in one embodiment is placed in a sealed vessel under controlled environment, e.g., temperature, pressure, and the like, simulating the environment encountered in wells, drilling, or in operation such as a power plant. In one embodiment, the device is placed into an autoclave under condition of the operating environment to be simulated, provided with monitoring probes, e.g., a pressure transducer, a temperature gauge, and the like. In another embodiment, it is set in an open environment. In a third embodiment, it is placed in a protective environment, e.g., a glove bag with an inert gas as the atmosphere, for the handling of corrosive materials such as magnesium chloride.

In one embodiment to use the device for stress corrosion testing, the test specimen is first mounted on the holder. The holder is rotated to lower the specimen in its position in the reservoir. In the next step, corrosive media is placed into the reservoir by methods known in the art and depending on the media being tested, e.g., with the use of a syringe, a beaker, etc. In one embodiment, just a sufficient amount of corrosive media is used to barely cover the stress point of the test specimen, e.g., a few millimeters above the lowest point of a C-ring or a U-bend specimen. In one embodiment, approximately 10 cc of a corrosive media is required for SCC testing of a C-ring test specimen having an inner diameter of about 38 mm, with the reservoir having a dimension of approximately 45 mm length by 23 mm width and 38 mm depth.

Reference will be made to the Figures, showing various embodiments of the testing device.

Figure 4A:
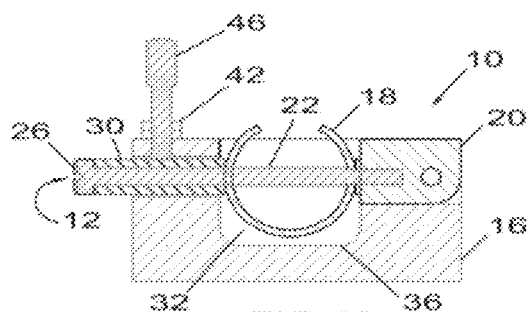
FIG. 4A is a cross-sectional view of one embodiment of a testing device along line A-A of FIG. 3A.
Figure 4B:
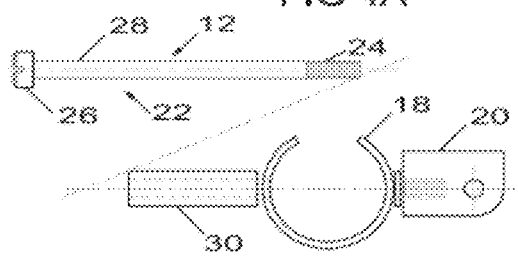
FIG. 4B is an assembly view of a holder of the testing device in FIG. 4A, as disassembled.
Figure 4C:
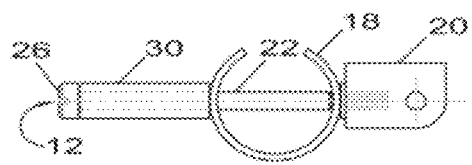
FIG. 4C is another assembly view of the holder of the testing device in FIG. 4A as assembled, with compressive stress being applied from outside of the test device.
Figure 5:
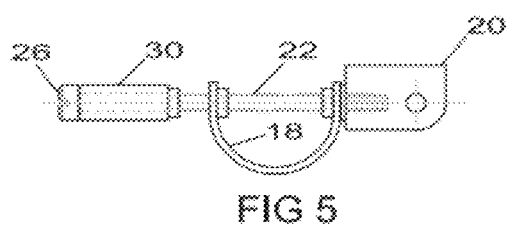
FIG. 5 is an assembly view of another embodiment of a holder, with compressive stress being applied from inside of the test device.
Figure 2:
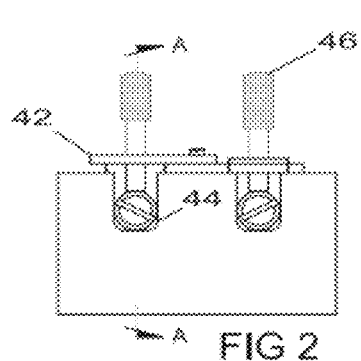
FIG. 2 is an end view of the testing device of FIG. 1.
Figures 3A, 3B, 3C:
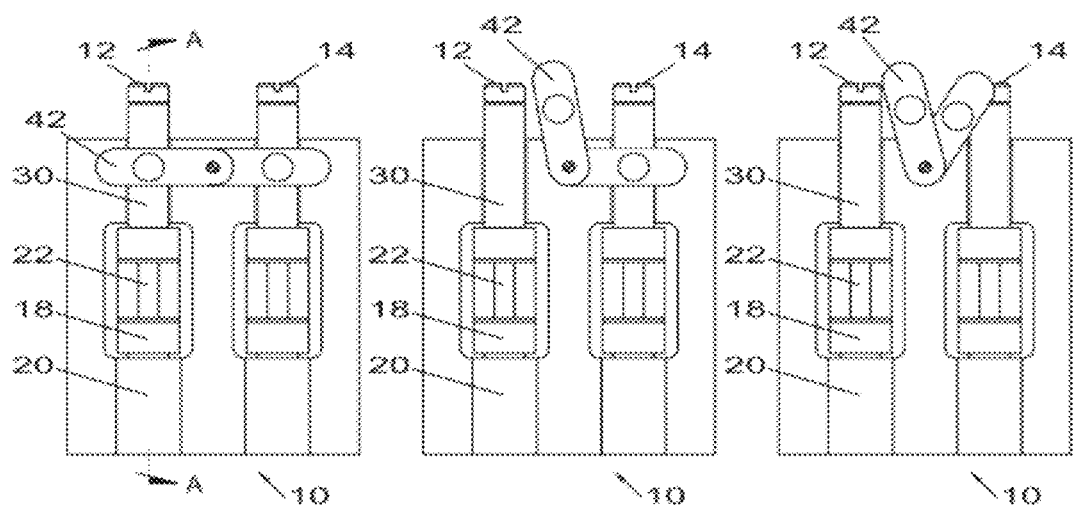
FIG. 3A is a top view of the testing device of FIG. 1 showing both locking mechanisms in an engaged position.
FIG. 3B is a top view of the testing device of FIG. 1 showing one locking mechanism in an engaged position and one locking mechanism in a disengaged position.
FIG. 3C is a top view of the testing device of FIG. 1 showing both locking mechanisms in a disengaged position.

As shown in FIG. 1, the testing device 10, includes two test specimen holders 12, 14 in a single base 16. In alternative embodiments, the device could include a single holder or, alternatively, include more than two holders for testing multiple samples. Multiple sample testing allows testing different medium or materials or confirmation of test data testing the same medium or material. The holders can also be of different sizes and/or for handling/testing test specimens of different configurations As shown, the holder 12 and the holder 14 share the same features. Therefore, only holder 12 will be described in greater detail. In FIGS. 2, 4, and 5, holder 12 is configured to secure and apply stress to a test specimen 18. The holder 12 includes a stop member 20, a shaft 22, and a sleeve 30. The stop member 20 is rotatably connected to the base 16 by a hinge such that the holder 12 pivots about a vertical axis, allowing the test specimen 18 to be lifted or lowered into the reservoir 32.

The shaft 22 includes a first end 24 configured to thread to the stop member 20, a second end 26 configured to engage with and receive torque from a hand tool, and a longitudinal body portion 28 between the first end 24 and second end 26 that is configured to extend through the test specimen 18. The sleeve 30 is configured to be positioned over the shaft 22 between the second end 26 and the test specimen 18. The holder 12 is configured such that threading the shaft 22 into the stop member 20 applies stress to the C-shaped specimen 18. It should be appreciated that many other alternative holder embodiment are possible. For example, in one alternative embodiment the holder could include a shaft with a first end 24 that is fixed to the stop 20 and a second end 26 that is threaded. In addition, the second end 26 could be configured to be hand tightened instead of tighten by a hand tool.

The base 16 includes a reservoir 32 configured to house test liquid. A retaining assembly connected to the based is configured to secure the holder above the reservoir. The holder 12 is connected to the base such that a specimen 18 secured in the holder 12 can be lowered into the (upper) opening of the reservoir 32 and secured in place relative to the reservoir 32.

In the embodiment as shown, the reservoir 32 is integral with the base and defines a recess therein. The reservoir 32 includes a bottom portion 36, surrounding side portions 38, and an open upper portion. The reservoir 32 is sized to receive a single test specimen. In another embodiment (not shown), it can be used to house a plurality of test specimens depending on the configuration of holder 20.

In the embodiment as shown, a retaining assembly 42 is optionally provided. The assembly 42 secures the holder 12 in place relative to the reservoir 32 for the testing of heavy corrosive media. The retaining assembly 42 includes a rest channel 44 and a knob 46 to hold down the holder. The rest channel 44 is configured to engage a portion of holder 12 when the holder is in its lowered position. In one embodiment instead of a knob, a latch (not shown) is employed to keep the holder in a locked down position. In one embodiment, the rest channel 44 is a U-shaped channel (support groove) that is integral with the base 16 and aligned with the shaft 22 near the second end 26. The bottom surface of the channel is raised relative to the bottom 36 of the reservoir 32 and is configured such that when the sleeve 30 of the holder 12 rests thereon, the shaft 22 of the holder is generally horizontal and a portion of the test specimen is near the bottom 36 of the reservoir.

In one embodiment the hinge connecting the stop member 20 to the base 16 is vertically adjustable (not shown). The channel 44 also has a plurality of vertical notches or grooves along the channel (not shown) corresponding to the adjustable hinged positions, allowing the stop member and the corresponding shaft to be positioned up or down relative to the base. The adjustable positions of the stop member in one embodiment accommodate test specimens of different heights and shapes.

In one embodiment, the retaining assembly 42 is configured such that the lowest portion of the test specimen is within millimeters from the bottom surface of the reservoir 32 when the holder 12 is secured in the retaining assembly 42, e.g., less than 10 mm, less than 5 mm, and less than 3 mm. It is desirable to keep the specimen as close to the bottom as possible to minimize the amount of corrosive media needed for testing.

The hold down 46 of the retaining assembly 42 is configured to pivot about a vertical axis from a release position to a locked position. The hold down can be any of a knob, a screw, or a latch, etc. In the locked position, the holder is held down on the rest 44 so that the holder is not free to pivot upwardly. In the release position, the holder is free to pivot about the horizontal axis that extends through the stop member 20. A portion of the shaft 22 at the second end 26 extends outside of the base 16. The portion serves as a handle for manipulating the position of the holder 12 relative to the base. It should be appreciated that many alternative hold down configurations are possible.

The illustrated figures include two test holders 12, 14 in a single base 16. The base includes two reservoirs and each of the reservoirs is associated with its own holder 12, 16. In alternative embodiments (not shown), the testing device can include multiple holders associated with a single continuous reservoir, multiple holders each associated with its own separate reservoir, or any combination of the above.

FIGS. 3A-3C and 6A-6D further illustrate a method of stress corrosion testing. First, a test specimen 18 is mounted onto test specimen holder 12. The holder 12 is lowered into the reservoir 32, thereby submerging a portion of the test specimen 18 in the reservoir. The holder 12 is secured in place to maintain the partially submerged position of the test specimen in the liquid reservoir 32. Corrosive medium can be added to the liquid reservoir (with the portion of the test specimen submerged within) before or after the application of stress onto the test specimen 18 with the tightening of the end 26.

In one embodiment, the step of applying stress to the test specimen 18 occurs after a portion of the test specimen is submerged in the liquid reservoir 32. Prior to submerging the text specimen, little or no stress is applied to the test specimen 18. In one embodiment, the step of mounting the test specimen 18 to the holder 12 includes extending a shaft 22 through the test specimen 18, wherein a portion of the shaft 22 includes a sleeve 30 thereon, and threading the shaft 22 to a stop member 20 that is pivotally connected to the liquid reservoir 32. In one embodiment, applying stress to the test specimen 18 includes rotating the shaft 22, thereby forcing the test specimen to be compressed between the stop member 20 and the sleeve 30. Although not shown, holder 12 in one embodiment is designed for accommodating a plurality of test specimen. In one embodiment, a plurality of sleeves are provided to separate the test specimen spaced apart. The specimen can be mounted by extending the shaft through the test specimens with the sleeves in between them, with at least one sleeve applying compressive stress on each specimen. In one embodiment, each specimen has two sleeves positioned on opposite sides of the test specimen for applying stress on both sides of the specimen.

Figure 7A:
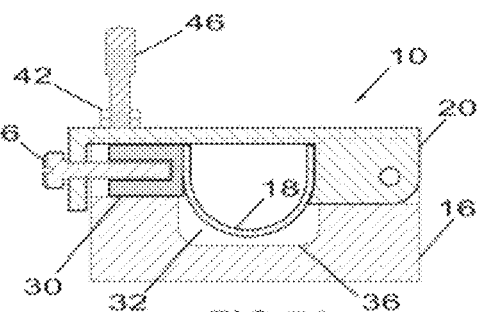
FIG. 7A is a cross-sectional view of another embodiment of a testing device, wherein the holder does not extend through the test specimen.
Figure 7B:
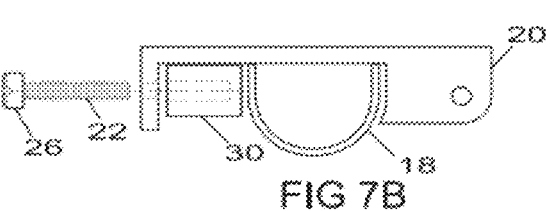
FIG. 7B is an assembly view of a holder in FIG. 7A, as disassembled.
Figure 7C:
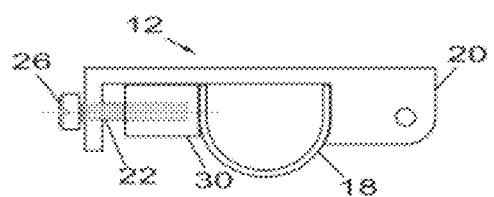
FIG. 7C is another assembly view of the holder in FIG. 7A, as assembled

FIGS. 5 and 7A-7C illustrate different embodiments of the holder 12 as well as methods for applying stress to the test specimen 18. In FIG. 5, sleeve nut 30 is used to apply compressive stress onto the specimen from the inside of the C-ring. Shaft 22 can be of varying length depending on the shape and size of the test specimen to be used. In FIGS. 7A-7C, the holder is designed such that the shaft 22 does not extend through the test specimen. The shaft functions to clamp a portion of the test specimen, e.g., the top of the specimen, as the test specimen is pushed against the first end of the shaft, with the sleeve nut 30 to applying stress against the test specimen 18 and holding it in place against the first end. In one embodiment (not shown), shaft 22 extends through the sleeve nut, with the sleeve nut 30 being used to apply stress against the test specimen and hold it stationary against the first end. In another embodiment, the shaft is provided with a plurality of sleeve nuts being of sufficient thickness to hold and compress a multitude of test specimen. The sleeve nuts function as spacings to separate the test specimen, with each test specimen being held stationary in place in-between two sleeve nuts positioned at opposite ends of the test specimen. After mounting the specimen, A Go-NoGo gauge can be used to check to see if the appropriate amount of stress is applied per specification, e.g., by checking the clearance "x" between the two bends of the C-ring or U-bend test specimen 18.

Figure 8:
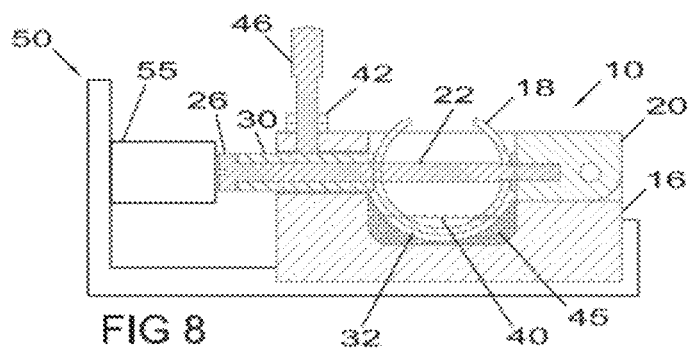
FIG. 8 is a cross-sectional view of one embodiment of a testing device with a reservoir having a contour configuration and a monitoring load cell.

FIG. 8 illustrates another embodiment of the test device in a test assembly 50, provided with a load cell 55 with a linear force sensing device or a distance sensing device (not shown) connected to the holder 12 via the second end 26. When the C-ring test specimen changes its state (no longer having the pre-determined distance "x" and/or under pre-set compressive stress), a sensing device such as a light or an alarm would go off, alerting a test operator that the test is over. Also as shown, the reservoir is provided with a removable liner 45 having a contour shape matching that with the test specimen. Only a minimal amount, e.g., 1 mm or so of the test medium is maintained over the lowest point of the C-ring, thus requiring a relatively small amount of corrosive medium to conduct the test.

Figure 9:
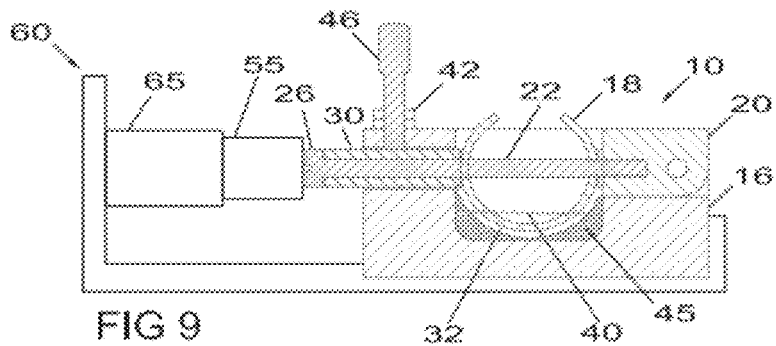
FIG. 9 is a cross-sectional view of another embodiment of the testing device of FIG. 8, with the addition of an automatic system to impose stress on the testing device.

In another embodiment as shown in FIG. 9, the test assembly 60 is provided with a stepper motor linear actuator 65 for exerting a pressure on the test holder 12 via the second end 26. The actuator is coupled to the load cell 55 for sensing any variations on the condition of the test specimen, e.g., pre-determined distance "x" and/or exerted stress on the specimen. In one embodiment, a constant pressure is imposed on the test specimen as it is exposed to the corrosion media. In another embodiment, the applied pressure can be varied, e.g., increased, over time.

The above specification, examples and data provide a description for the manufacture and use of the invention. It should be appreciated that many other alternative embodiments are possible. Since many embodiments of the invention can be made without departing from the spirit and scope of the invention, the invention resides in the claims hereinafter appended.

I claim:

1. A method of testing stress corrosion cracking of a test specimen in a corrosive media, the method comprising:
   providing a test specimen;
   providing a test device having: a base configured to house a reservoir for containing the corrosive media and a holder configured to secure the test specimen, the holder includes at least a sleeve to secure the test specimen in place and apply compressive stress against the test specimen, the holder is rotatably connected to the base to lower the test specimen into the reservoir;
   mounting the test specimen onto the holder;
   pivoting the holder towards the reservoir to lower at least a portion of the test specimen in the reservoir;
   adjusting the sleeve to apply a sufficient amount of stress on the test specimen; and
   filling the reservoir with a sufficient amount of the corrosive media for stress corrosion testing.

2. The method of claim 1, wherein the step of adjusting the sleeve to apply stress to the test specimen occurs after at least a portion of the test specimen is lowered into the reservoir.

3. The method of claim 1, wherein the step of adjusting the sleeve to apply stress to the test specimen occurs before the test specimen is lowered into the reservoir.

4. The method of claim 1, wherein the step of filling the reservoir with the corrosive media occurs before adjusting the sleeve to apply stress to the test specimen.

5. The method of claim 1, wherein the step of filling the reservoir with the corrosive media occurs after stress is applied onto the test specimen.

6. The method of claim 1, further comprising using a go/nogo gauge to check the test specimen verifying the amount of stress.

7. The method of claim 1, further comprising connecting the holder to a load cell for sensing a change in the compressive stress against the test specimen.

8. The method of claim 1, further comprising connecting the holder to a linear actuator for exerting a force onto the test specimen via the test holder.

9. The method of claim 1, wherein the holder includes a shaft and a stop member that pivotally connects the holder to the base, and the step of mounting the test specimen to the holder includes extending the shaft through the test specimen and threading the shaft to the stop member.

10. The method of claim 9, wherein the shaft includes a first end and a second end with a sleeve, and the step of applying stress to the test specimen includes rotating the shaft to thread the first end into the stop member, thereby forcing the test specimen to be compressed between the stop member and the sleeve.

11. A method of testing stress corrosion cracking of a test specimen in a corrosive media, the method comprising:
   providing a test specimen;
   providing a test device having: a base configured to house a reservoir for containing the corrosive media, a holder configured to secure the test specimen, and a retaining assembly rotatably connected to the base and configured to secure the holder above the reservoir, the holder includes a sleeve to secure the test specimen in place and apply compressive stress against the test specimen, the holder is rotatably connected to the base to lower the test specimen into the upper opening of the reservoir;
   mounting the test specimen to the holder;
   pivoting the holder towards the reservoir to submerge a portion of the test specimen in the reservoir;
   rotating the retaining assembly to lock the holder in a stationary position in the reservoir;
   adjusting the sleeve to apply a sufficient amount of stress on the test specimen; and
   filling the reservoir with a sufficient amount of the corrosive media for stress corrosion testing.

12. The method of claim 11, wherein the corrosive media for filling the reservoir has a density that is higher than the density of the test specimen.

13. The method of claim 11, wherein the holder includes a stop member and a shaft, and the step of mounting the test specimen to the test holder includes extending the shaft through the test specimen and threading the shaft to the stop member that pivotally connects the holder to the base.

14. The method of claim 11, wherein the shaft includes a first end and a second end with a sleeve, and the step of applying stress to the test specimen includes rotating the shaft to thread the first end into the stop member, thereby forcing the test specimen to be compressed between the stop member and the sleeve.

15. The method of claiming 11, further comprising providing a reservoir with an opening for containing the corrosive media and placing the reservoir into the base before filling the reservoir with the corrosive media.

16. A method of testing stress corrosion cracking of a test specimen in a corrosive media, the method comprising:
   providing a test specimen;
   providing a test device having: a base configured with a basin to house a reservoir, a holder configured to secure at least the test specimen, the holder includes at least a sleeve to secure the test specimen in place and apply compressive stress against the test specimen, the holder is rotatably connected to the base to lower the test specimen into the reservoir;
   providing a reservoir with an opening for containing the corrosive media;
   placing the reservoir into the basin;
   mounting the test specimen onto the holder;
   pivoting the holder towards the reservoir to lower at least a portion of the test specimen in the reservoir;
   adjusting the sleeve to apply a sufficient amount of stress on the test specimen; and
   filling the reservoir with a sufficient amount of the corrosive media for stress corrosion testing.

17. The method of claim 16, wherein the holder includes shaft having a first end portion and a second end portion having a sleeve for applying stress against the test specimen, holding it in place against the first portion of the shaft when the sleeve is rotated.

18. The method of claim 16, further comprising using a go/nogo gauge to check the test specimen verifying the amount of stress.

19. The method of claim 16, further comprising connecting the holder to a load cell for sensing a change in the compressive stress against the test specimen.

20. The method of claim 16, further comprising connecting the holder to a linear actuator for exerting a force onto the test specimen via the test holder.

* * * * *